United States Patent
Har-Noy

(10) Patent No.: US 9,320,794 B2
(45) Date of Patent: *Apr. 26, 2016

(54) ABLATIVE IMMUNOTHERAPY

(71) Applicant: Immunovative Therapies Ltd., Jerusalem (IL)

(72) Inventor: Michael Har-Noy, Modi'in (IL)

(73) Assignee: IMMUNOVATIVE THERAPIES, LTD., Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 13/796,171

(22) Filed: Mar. 12, 2013

(65) Prior Publication Data

US 2013/0189301 A1 Jul. 25, 2013

Related U.S. Application Data

(60) Continuation-in-part of application No. 13/150,893, filed on Jun. 1, 2011, which is a division of application No. 11/936,948, filed on Nov. 8, 2007, now Pat. No. 7,972,594.

(60) Provisional application No. 60/858,507, filed on Nov. 13, 2006.

(51) Int. Cl.

| *A61K 35/12* | (2015.01) |
|---|---|
| *A61K 41/00* | (2006.01) |
| *A61B 18/02* | (2006.01) |
| *A61B 18/12* | (2006.01) |
| *A61K 35/17* | (2015.01) |
| *A61K 39/00* | (2006.01) |

(52) U.S. Cl.
CPC .......... *A61K 41/0028* (2013.01); *A61B 18/02* (2013.01); *A61B 18/12* (2013.01); *A61K 35/17* (2013.01); *A61K 2039/57* (2013.01)

(58) Field of Classification Search
None
See application file for complete search history.

(56) References Cited

U.S. PATENT DOCUMENTS

| 5,837,251 | A | 11/1998 | Srivastava |
|---|---|---|---|
| 6,136,315 | A | 10/2000 | Srivastava |
| 6,139,841 | A | 10/2000 | Srivastava |
| 6,162,436 | A | 12/2000 | Srivastava |
| 6,187,312 | B1 | 2/2001 | Srivastava |
| 6,277,368 | B1 | 8/2001 | Hiserodt et al. |
| 6,797,480 | B1 | 9/2004 | Srivastava |
| 6,875,849 | B2 | 4/2005 | Graner et al. |
| 7,435,592 | B2 | 10/2008 | Har-Noy |
| 7,678,572 | B2 | 3/2010 | Har-Noy |
| 7,972,594 | B2 | 7/2011 | Har-Noy |
| 2005/0214268 | A1* | 9/2005 | Cavanagh et al. ......... 424/93.21 |
| 2008/0112963 | A1 | 5/2008 | Har-Noy |

OTHER PUBLICATIONS

Machlenkin et al (Cancer Research, 2005, 11:4955-4961).*
Ganss et al (Cancer Research, 2002, 62:1462-1470).*
Ablin, R. J., G. Fontana, et al. (1982). "Cryoimmunotherapy: a conference report." Eur Surg Res 14(4): 309-16.
Agrewala, J.N. et al., "Delivery of antigen in allogeneic cells preferentially generates DC4+Th1 cells", Clinical and Experimental Immunology, 2003, vol. 134, pp. 13-22.
Banchereau, J., F. Briere, et al. (2000). "Immunobiology of dendritic cells." Annu Rev Immunol 18: 767-811.
Banchereau, J. and R. M. Steinman (1998). "Dendritic cells and the control of immunity." Nature 392(6673): 245-52.
Bell, D., J. W. Young, et al. (1999). "Dendritic cells." Adv Immunol 72: 255-324.
Berzofsky, J. A., J. D. Ahlers, et al. (2004). "Progress on new vaccine strategies against chronic viral infections." J Clin Invest 114(4): 450-62.
Berzofsky, J. A., M. Terabe, et al. (2004). "Progress on new vaccine strategies for the immunotherapy and prevention of cancer." J Clin Invest 113(11): 1515-25.
Bishop et al., "Allogeneic lymphocytes induce tumor regression of advanced metastatic breast cancer." Journal of Clinical Oncology, 2004, vol. 22, No. 19, pp. 3886-3892.
Boon, T., J. C. Cerottini, et al. (1994). "Tumor antigens recognized by T lymphocytes." Annu Rev Immunol 12: 337-65.
Devarapu, S.K. et al., "Triggering of T cell-meidated immune responses by allogenic tumor cell vaccine in patients with oral cancer", Immunopharmacology and Immunotoxicology, 2006, vol. 28, pp. 387-395.
Eibl et al., "Evidence for a graft-versus-tumor effect in a patient treated with marrow ablative chmotherapy and allogeneic bone marrow transplantation of breast cancer", Blood, 1996, vol. 88, No. 4, pp. 1501-1508.
Encke, J. et al., "Prophylactic and therapeutic vaccination with dendritic cells against hepatitis C virus infection", Clinical and Experimental Immunology, 2005, vol. 142, pp. 362-269.
Fujii, S., K. Liu, et al. (2004). "The linkage of innate to adaptive immunity via maturing dendritic cells in vivo requires CD40 ligation in addition to antigen presentation and CD80/86 costimulation." J Exp Med 199(12): 1607-18.

(Continued)

*Primary Examiner* — Laura B Goddard
(74) *Attorney, Agent, or Firm* — Westman, Champlin & Koehler, P.A.; Z. Peter Sawicki; Visala C. Goswitz

(57) ABSTRACT

The disclosure herein relates generally to immunotherapy and, more specifically, to the use of immunotherapy for treating tumors and pathogen infected tissues. The immunotherapy relates to first priming patients with allogeneic cells designed to be rejected by a Th1 mediated mechanism, then inducing in situ necrosis or apoptosis in a tumor or pathogen infected lesion. Necrosis or apoptosis can be induced by methods such as cryotherapy, irreversible electroporation, chemotherapy, radiation therapy, ultrasound therapy, ethanol chemoablation, microwave thermal ablation, radiofrequency energy or a combination thereof applied against at least a portion of the tumor or pathogen infected tissue. One or more doses of allogeneic cells (e.g., Th1 cells) are then delivered within or proximate to the tumor or pathogen-infected tissue in the primed patient. The present invention provides an immunotherapeutic strategy to develop de-novo systemic (adaptive) immunity to a tumor or pathogen.

6 Claims, No Drawings

(56) References Cited

OTHER PUBLICATIONS

Gallucci, S., M. Lolkema, et al. (1999). "Natural adjuvants: endogenous activators of dendritic cells." Nat Med 5(11): 1249-55.

Gazzaniga, S., A. Bravo, et al. (2001). "Inflammatory changes after cryosurgery-induced necrosis in human melanoma xenografted in nude mice." J Invest Dermatol 116(5): 664-71.

Gong, J. et al., "Fusions of human ovarian carcinoma cells with autologous or allogeneic dendritic cells induced antitumor immunity", The Journal of Immunology, 2000, vol. 165, pp. 1705-1711.

Knutson, K. L. and M. L. Disis (2004). "IL-12 enhances the generation of tumour antigen-specific Th1 CD4 T cells during ex vivo expansion." Clin Exp Immunol 135(2): 322-9.

Machlenkin et al., "Combined dendritic cell cryotherapy of tumor induces systemic antimetastatic immunity", Clin. Cancer Res., 2005, vol. 11, No. 13, pp. 4955-4961.

Matzinger, P. (2002). "The danger model: a renewed sense of self." Science 296(5566): 301-5.

Matzinger, P. (2002). "An innate sense of danger." Ann N Y Acad Sci 961: 341-2.

Mazur, P. (1984). "Freezing of living cells: mechanisms and implications." Am J Physiol 247(3 Pt 1): C125-42.

Melcher et al., "Adoptive transfer of immature dendritic cells with autologous or allogeneic tumor cells generates systemic antitumor immunity", Cancer Research, 1999, vol. 59, pp. 2802-2805.

Orpwood, R. D. (1981). "Biophysical and engineering aspects of cryosurgery." Phys Med Biol 26(4): 555-75.

Ostrowski, M. A., Q. Yu, et al. (2006). "Why can't the immune system control HIV-1? Defining HIV-1-specific CD4+ T cell immunity in order to develop strategies to enhance viral immunity." Immunol Res 35(1-2): 89-102.

O'Sullivan, B. and R. Thomas (2003). "CD40 and dendritic cell function." Crit Rev Immunol 23(1-2): 83-107.

Pardoll, D. M. (2002). "Spinning molecular immunology into successful immunotherapy." Nat Rev Immunol 2(4): 227-38.

Reis e Sousa, C. (2001). "Dendritic cells as sensors of infection." Immunity 14(5): 495-8.

Rosenberg, S. A. (2004). "Development of effective immunotherapy for the treatment of patients with cancer." J Am Coll Surg 198(5): 685-96.

Rubinsky, B. et al. (2007). "Irreversible Electroporation: A New Ablation Modality—Clinical Implications." Technology in Cancer Research and Treatment, vol. 6, No. 1, pp. 1-12.

Sauter, B., M. L. Albert, et al. (2000). "Consequences of cell death: exposure to necrotic tumor cells, but not primary tissue cells or apoptotic cells, induces the maturation of immunostimulatory dendritic cells." J Exp Med 191(3): 423-34.

Segal, B. H., X. Y. Wang, et al. (2006). "Heat shock proteins as vaccine adjuvants in infections and cancer." Drug Discov Today 11(11-12): 534-40.

Shi, Y., W. Zheng, et al. (2000). "Cell injury releases endogenous adjuvants that stimulate cytotoxic T cell responses." Proc Natl Acad Sci U S A 97(26): 14590-5.

Thimme, R., V. Lohmann, et al. (2006). "A target on the move: innate and adaptive immune escape strategies of hepatitis C virus." Antiviral Res 69(3): 129-41.

Waldmann, T. A. (2003). "Immunotherapy: past, present and future." Nat Med 9(3): 269-77.

PCT Search Report and Written Opinion for PCT/US2014/022287, mailed Aug. 14, 2014.

* cited by examiner

ABLATIVE IMMUNOTHERAPY

CROSS-REFERENCE TO RELATED APPLICATION

The present application is a continuation-in-part and claims priority to U.S. patent application Ser. No. 13/150,893, which is a divisional of and claims priority of U.S. patent application Ser. No. 11/936,948, filed Nov. 8, 2007, now U.S. Pat. No. 7,972,594, the content of which is hereby incorporated by reference in its entirety, which claims the benefit of U.S. provisional patent application Ser. No. 60/858,507, filed Nov. 13, 2006, the content of which is hereby incorporated by reference in its entirety.

FIELD

The present disclosure relates generally to immunotherapy and, more specifically, to therapeutic methods and compositions for treating tumors and pathogen infected tissues.

BACKGROUND

Harnessing the power of the immune system to treat chronic infectious diseases or cancer is a major goal of immunotherapy. Active immunotherapy treatments are methods designed to activate the immune system to specifically recognize and destroy tumor or pathogen-infected cells. For over 200 years active immunotherapy approaches have been used to prevent numerous infectious diseases, including small pox, rabies, typhoid, cholera, plague, measles, varicella, mumps, poliomyelitis, hepatitis B and the tetanus and diphtheria toxins.

Active immunotherapy concepts are now being applied to develop therapeutic cancer vaccines with the intention of treating existing tumors or preventing tumor recurrence as well as for treatment and prevention of chronic viral infection. Many of these techniques have proven to successfully develop increased frequencies of immune cells in circulation that have the ability to specifically kill tumors or pathogen infected cells. However, despite the ability to generate immune cells reactive against tumor antigens, tumor escape mechanisms can overpower this immune response resulting in eventual tumor progression.

Active immunotherapy of cancer has been shown to be very effective in numerous rodent models. However, the clinically disappointing results of decades of immunotherapy trials of various types in humans have shown the immune system in humans does not perceive the threat/danger of human cancer cells as well as the immune system of rodent models of the same diseases.

The same is true of chronic viral infection. The innate immune response is able to slow down viral replication and activate cytokines which trigger the synthesis of antiviral proteins. The adaptive immune system neutralizes virus particles and destroys infected cells. However, viruses have developed a number of countermeasures to avoid immune attack and stay moving targets for the immune system.

There is a need to provide an active immunotherapy that is capable of overcoming tumor and viral immunoavoidance mechanisms and to train the human immune system to perceive the threat/danger of human cancer cells and viral infected cells resulting in an immune response which can eradicate tumors or pathogen-infected cells wherever they might be located in the body.

SUMMARY

The present disclosure relates to methods and compositions for inducing a systemic, adaptive immune response against a tumor or pathogen. The method uses a combination of an allogeneic cell therapy and a method for subjecting the tumor or pathogen infected tissue to cellular distress, resulting in the liberation of tumor specific antigen(s) or pathogen specific antigen(s).

In one aspect, the present disclosure is a method for inducing an adaptive immune response against a tumor or a pathogen in a subject. The method includes the steps of: (1) administering to a subject with cancer or an infectious disease an aliquot of allogeneic cells that are designed to be rejected by the subject immune system in a manner that induces anti-allogeneic Th1 immunity; (2) in the same subject, after allowing time for an anti-allogeneic Th1 immune memory to form (about 7 to 14 days), performing an in situ ablation of an accessible tumor lesion or pathogen-infected tissue with an ablation method which causes at least a portion of the tumor or infected tissue to die, preferably by necrosis, (e.g., by methods such as but not limited to electroporation, cryoablation, chemotherapy, radiation therapy, ultrasound therapy, ethanol chemoablation, microwave thermal ablation, radiofrequency energy or a combination thereof); then; (3) injecting a second aliquot of the same allogeneic cells intralesionally (same cells as used to prime), preferably 2-24 hrs after the ablation step, creating an immune response that serves as an adjuvant to the uptake of antigen(s) and the subsequent maturation of host antigen presenting cells (i.e., dendritic cells) responding to the necrotic or apoptotic tissue. Mature antigen presenting cells from the lesion then migrate to the lymph nodes and stimulate systemic anti-tumor or anti-pathogen immunity. In another aspect, the priming step is omitted. The tissue from the tumor or the pathogen infected tissue is ablated in situ and an aliquot of the allogeneic cells are injected after the ablation to create the desired immune response.

In another aspect, the present disclosure includes a vaccine for a patient against a tumor or a pathogen. The vaccine includes an antigenic composition comprising antigenic material from the tumor or pathogen and an aliquot of allogeneic cells wherein administration of the antigenic composition to the patient creates a rejection response and stimulates a delayed-type hypersensitivity response to the antigens thereby acting as an adjuvant to the stimulation of systemic anti-tumor or anti-pathogen immunity in the patient. The vaccine can also include a priming composition wherein the priming composition includes an aliquot of allogeneic cells.

In yet another aspect, the present disclosure includes a method of vaccinating a patient. The method includes the steps of: (1) administering to the subject with cancer or an infectious disease a priming composition that includes an aliquot of allogeneic cells that are designed to be rejected by the subject immune system in a manner that induces anti-allogeneic Th1 immunity; (2) in the same subject, after allowing time for an anti-allogeneic Th1 immune memory to develop (about 7 to 14 days), injecting, preferably intradermally, an antigenic composition containing a source of tumor antigen or pathogen antigens (e.g., attenuated virus, tumor lysates, heat shock proteins), preferably containing from the same individual autologous lysates of the infected or cancerous tissue, the lysates preferably containing chaperone proteins, and such lysates formulated with an aliquot of allogeneic cells (same cells used to prime the patient) to create a rejection response and stimulate a delayed-type hypersensitivity response to the alloantigens which serve to adjuvant the stimulation of systemic anti-tumor or anti-pathogen immunity. In a further aspect, this method may be practiced without the priming step.

In another aspect, the present disclosure includes a therapeutic composition for treating a tumor or a pathogen in a patient comprising tumor antigens or pathogen antigens generated in situ and allogeneic cells, wherein the allogeneic cells and the in situ generated antigens elicit an immune response whereby subsequent maturation of the patient's antigen presenting cells systemically stimulate anti-tumor or anti pathogen immunity. The tumor antigens or pathogen antigens are generated in situ from necrosis of the tumor or the pathogen infected tissue. The therapeutic composition may also include a priming composition containing allogeneic cells. The allogeneic cells in the priming composition and in the antigenic composition may include between about $1\times10^8$ and about $1\times10^{10}$ cells.

In yet a further aspect, the present description includes a vaccine composition for treating a tumor or a pathogen in a patient comprising antigens generated in situ that include tumor antigens or pathogen antigens and allogeneic cells wherein injecting the patient with the allogeneic cells in the presence of in situ generated antigens creates an immune response whereby subsequent maturation of the patient's antigen presenting cells systemically stimulate anti-tumor or anti pathogen immunity. The tumor antigens in the composition are derived from in situ necrosis of the tumor. The pathogen antigens in the composition are derived from in situ necrosis of the pathogen infected tissue. The composition may also include a priming composition containing allogeneic cells. The allogeneic cells in the priming composition and in the vaccine composition may include between about $1\times10^8$ and about $1\times10^{10}$ cells.

In a further aspect, the present disclosure includes a method of vaccinating a patient. The method includes the steps of: (1) administering to the subject with cancer or an infectious disease a priming composition that includes an aliquot of allogeneic cells that are designed to be rejected by the subject immune system in a manner that induces anti-allogeneic Th1 immunity; (2) in the same subject, after allowing time for an anti-allogeneic Th1 immune memory to develop (about 7 to 14 days), ablating the tumor or pathogen infected tissue in situ to release tumor antigens or pathogen antigens (3) administering a composition of allogeneic cells (same cells used to prime the patient) to create a rejection response and stimulate a delayed-type hypersensitivity response to the alloantigens which serve to adjuvant the stimulation of systemic anti-tumor or anti-pathogen immunity. In a further aspect, this method may be practiced without the priming step.

DETAILED DESCRIPTION OF ILLUSTRATIVE EMBODIMENTS

The present disclosure includes a method for stimulating anti-tumor or anti-pathogen immunity in patients. The method involves first "priming" of the patient to develop Th1 anti-alloantigen immune memory by infusion of an aliquot of allogeneic cells. It is desired that the infusion of allogeneic cells stimulates the patient's immune system to react against the allogeneic cells. A time period is allowed to elapse until the patient's immune system is allowed to form an anti-allogeneic memory. In some embodiments, a patient may need a booster of allogeneic cells to develop the appropriate Th1 immune memory.

Patient as used herein includes not only mice but also humans. Th1 response as used herein refers to production of a cytokine profile that activates T-cells and macrophages. Th1 response is to be distinguished from Th2 response which activates mainly an immune response that depends upon antibodies and is antagonistic to the Th1 response.

The next step includes injury and/or death of cells within a tumor bed or pathogen-infected tissue after the patient develops sufficient anti-allogeneic Th1 immune memory. Tissue injury or death releases cellular components and recruits scavenger cells to the injury site. The release of cellular components during tissue injury or tissue death by necrosis is critical for the in situ generation of tumor or pathogen antigens. A variety of methods are known in the art to cause tissue injury or death within a tumor bed or pathogen infected tissue. Preferably death is by necrosis, which causes recruitment of scavenger cells to the injury site. In some preferred embodiments, tissue death or injury is by cryoablation or by irreversible electroporation. Alternatively, tissue is ablated ex-vivo and the released components injected into the patient.

The scavenger cells, including immature dendritic cells can pick up antigens released from the damaged or dead tissues. A second aliquot of allogeneic cells are injected intralesionally in order to cause the maturation of dendritic cells (DC) for the priming of Th1 immunity to the antigens. By intralesionally is meant administration of the composition of this invention through injection or otherwise directly into a cancerous area or tumor or a pathogen infected tissue. In preferred embodiments, all of the allogeneic cells administered to the patient are from the same source. Preferably, the allogeneic cells are administered between about 2 and about 24 hours after ablation of the tissue. This method is especially useful in the treatment of solid or metastatic tumors, particularly in patients with tumor lesions resident in the prostate, breast, bone, liver, lung, or kidney.

It is desirable for the patient to develop a strong delayed-type hypersensitivity (DTH) reaction upon introduction of the second aliquot of allogeneic cells resulting in rejection of the allogeneic cells due to the fact that the patient has been primed to Th1 immunity against the allogeneic cells introduced by the first aliquot. The by-stander effect of the anti-alloantigen DTH reaction can produce "danger signals" which serve to cause the DC, collecting and processing antigens from the damaged tissue, to mature and migrate to the draining lymph nodes. The combination of the induction of tissue injury and the DTH rejection response can create an inflammatory environment which leads to Th1 immunity against the antigens released from the damaged tissue.

The general state of inflammation caused by the treatment process can serve to cause the DC to program T-cells to Th1 immunity against antigens in the damaged tissue resulting in a systemic adaptive immune response to the tumor or pathogen-infected cells and the disabling of tumor and pathogen-mediated immune avoidance mechanisms. By adaptive immunity is meant that the patient's defenses are mediated by B and T cells following exposure to antigen and that such defenses exhibit specificity, diversity, memory, and self/non-self recognition. Such adaptive immunity is systemic within the patient. Adaptive immunity is to be distinguished from innate immunity which is non-specific and exists prior to exposure to the antigen.

In some embodiments, ablation followed by administration of the allogeneic cells may be sufficient to generate the desired response. In other words, the priming of the patient by a first aliquot of allogeneic cells may be omitted. In these embodiments, tissue from the tumor or infected by a pathogen is ablated followed by injection of an aliquot of allogeneic cells.

The present invention also includes a method of vaccinating a patient having cancerous cells or an infected tissue. This method can be used to vaccinate a patient using in situ generated antigens from the cancerous cells or infected tissue in conjunction with administration of allogeneic cells. This method can also be used for patients with hematological malignancies, (e.g., Chronic Lymphocytic Leukemia, Multiple Myeloma, and non-Hodgkin's lymphomas) or viral infectious diseases (e.g., hepatitis B or C, herpes, HIV) and other disorders where the affected lesions are not easily assessable for ablation.

The method involves first "priming" of the patient to develop Th1 anti-alloantigen immune memory by infusion of a first aliquot of allogeneic cells. It is desired that the infusion of allogeneic cells stimulates the patient's immune system to react against the allogeneic cells. A time period is allowed to elapse until the patient's immune system is allowed to form an anti-allogeneic memory. In some embodiments, a patient may need a booster of allogeneic cells to develop the appropriate Th1 immune memory.

The next step includes exposing the patient's immune system to antigens from the cancerous cells or the pathogen infected tissue in addition to the activated allogeneic cells described herein. In preferred embodiments, the antigens are generated in situ by ablation of the cancerous cells/tumors or the pathogen infected tissue. In situ ablation of the tumors or the pathogen infected tissue results in the release of tumor antigens or pathogen antigens in the patient. The subsequent administration of the allogeneic cells at site of the lesion results in the desired immune response by creating a rejection response in the patient and stimulating a delayed-type hypersensitivity response to the antigens. The ablation can be by cryoablation, electroporation or other means that result in necrotic death of tumors or pathogen infected tissue In other embodiments, after the priming step, the method can include administering into the patient an antigenic composition that includes an autologous lysate containing antigens from the cancerous cells or the infected tissue. This composition also includes an aliquot of the allogeneic cells, i.e. allogeneic cells that are from the same source as the allogeneic cells used in the priming step. The injection of the antigenic composition can create a rejection response in the patient and can stimulate a delayed-type hypersensitivity response to the antigens.

The scavenger cells, including immature dendritic cells can pick up the antigens resulting from the in situ ablation or from the autologous lysate. The allogeneic cells can cause the maturation of dendritic cells for the priming of Th1 immunity to the antigens. It is desirable for the patient to develop a strong DTH reaction upon introduction of the allogeneic cells at the site of the necrotic lesion due to the fact that the patient has been primed to Th1 immunity against the allogeneic cells introduced by the first aliquot of allogeneic cells during the priming step.

The general state of inflammation caused by the treatment process can serve to cause the DC to program T-cells to Th1 immunity against the antigens at the ablation site resulting in a systemic adaptive immune response to the tumor or pathogen-infected cells and the disabling of tumor and pathogen-mediated immune avoidance mechanisms.

The present disclosure also provides a method for enhancing the immunogenicity of weakly immunogenic or non-immunogenic tumors and a method to deviate an immune response from a non-protective immune response (e.g., Th2 response) to a protective immune response (e.g., Th1). Such diseases include, for example, all types of cancers and diseases caused by infections with a variety of pathogens (e.g., Hepatitis viruses, fungal infections such as aspergillus, HIV, malaria, typhoid, cholera, herpes viruses, Chlamydia, and HPV).

The present disclosure also includes a therapeutic composition for treating a tumor or a pathogen in a patient. The therapeutic composition preferably includes allogeneic cells and antigens, generated in situ, comprising the products of tumor necrosis or pathogen infected tissue necrosis. The therapeutic composition may also include a priming composition. The priming composition generally contains allogeneic cells that are injected into the patient to generate a rejection response by the patient's immune system in a manner that induces an allogeneic Th1 immunity.

The therapeutic composition includes antigenic material from the tumor or pathogen-infected tissue and an aliquot of allogeneic cells. In preferred embodiments, the antigenic material is in situ released antigenic material containing antigens from the cancerous cells or from infected tissue. The antigenic material can be derived in situ from tissue necrosis of the tumor or the pathogen-infected tissue. Preferably, the antigenic material is derived from ablation of the tumor or pathogen-infected tissue.

The ablation may be done in vivo, in situ or ex vivo. In some embodiments, the antigenic material includes heat shock proteins released upon ablation of the tissue from a tumor or pathogen-infected tissue.

The therapeutic composition also includes allogeneic cells. In embodiments with in situ generated antigenic material, the therapeutic composition includes allogeneic cells that are administered directly into the lesion site containing the in situ generated antigens. The allogeneic cells, when injected into the patient, can create a rejection response and stimulate a delayed-type hypersensitivity response to the antigens thereby acting as an adjuvant to the stimulation of systemic anti-tumor or anti-pathogen immunity in the patient.

The therapeutic compositions may include other components that act as adjuvants to the response generated by the priming composition and the allogeneic cells. The priming composition and allogeneic cells may include other components generally found in therapeutic composition, for example, preservatives. The addition of these components are within the scope of this invention.

In some embodiments, the therapeutic composition may only include the allogeneic cells and in situ generated antigens and not the priming composition. The priming composition may not be needed to obtain the desired immune response.

The present invention also includes a vaccine composition for a patient against a tumor or a pathogen. The vaccine preferably includes a priming composition and an antigenic composition. The priming composition generally contains allogeneic cells which are injected into the patient to generate a rejection response by the patient's immune system in a manner that induces an allogeneic Th1 immunity.

The antigenic composition includes antigenic material from the tumor or pathogen-infected tissue and an aliquot of allogeneic cells. In some embodiments, the antigenic material is an autologous lysate containing antigens from the cancerous cells or from infected tissue. The antigenic material can be derived from tissue necrosis of the tumor or the pathogen-infected tissue. Preferably, the antigenic material is derived from ablation of the tumor or pathogen-infected tissue. The ablation may be done in vivo or ex vivo. In some embodiments, the antigenic material includes heat shock proteins released upon ablation of the tissue from a tumor or pathogen-infected tissue. The antigenic composition also includes allogeneic cells. The antigenic material and the allogeneic cells may be combined together or packaged separately.

The present disclosure also includes an in situ generated vaccine composition. The antigenic material in this vaccine is generated in situ and the allogeneic cells are administered to the patient as an adjuvant, preferably intralesionally. The in situ generation of antigenic material can be accomplished by ablation of the tumor or pathogen infected tissue within the patient releasing the antigenic material. The ablation can be by cryoablation, electroporation or other means that result in necrotic death of tumors or pathogen infected tissue.

In embodiments with in situ generated antigens, the antigenic composition administered to the patient includes allogeneic cells and these cells are administered at the necrotic lesion site containing the released antigens. The antigenic composition, when injected into the patient, can create a rejection response and stimulate a delayed-type hypersensitivity response to the antigens thereby acting as an adjuvant to the stimulation of systemic anti-tumor or anti-pathogen immunity in the patient.

The vaccine may include other components that act as adjuvants to the response generated by the priming composition and the antigenic composition. The priming composition and antigenic composition may include other components generally found in vaccines, for example, preservatives. The addition of these components are all within the scope of this invention.

In some embodiments, the vaccine may only include the antigenic composition and not the priming composition. The antigenic composition may be sufficient to obtain the desired immune response.

The therapeutic vaccines of the present invention are useful for the prevention and treatment of diseases such as cancer or chronic viral diseases that develop and/or persist by suppressing or escaping the immune response.

Priming Step

The purpose of the priming step is to create anti-allogeneic Th1 immunity in a patient that can be recalled upon subsequent exposure to the alloantigens. Priming occurs by exposing a patient to an aliquot of allogeneic cells and the subsequent rejection of these allogeneic cells when a second aliquot is administered to the patient by the patient's immune system resulting from immune memory. Preferably, the patients are not immunosuppressed prior to priming, as this will inhibit the ability of the patient to reject the infused allogeneic cells and will also inhibit the development of anti-alloantigen Th1 immunity.

In one embodiment of the present invention, the patient's immune system is skewed to generate Th1 immunity. It is preferable to manipulate the allogeneic cells such that Th1 and not Th2 immunity develops in response to the rejection of the allogeneic cells. In one embodiment, the patient's immune system can be skewed to produce Th-1 response by administering allogeneic cells that are producing Th1 cytokines (e.g., IFN-gamma and TNF-alpha) when infused. Th1 cytokines can assist in skewing the immune response to the alloantigens to Th1 type immunity. Other methods of skewing a patient's immune system to produce Th-1 immunity are also within the scope of this invention.

The allogeneic cells used to first prime the patients and then later used for either intralesional administration (after induction of cell death) or as an adjuvant to a source of pathogenic or tumor material, are preferably allogeneic activated T-cells, more preferably allogeneic activated CD4+ Th1 cells, more preferably allogeneic CD4+ T-cells that have differentiated into effector or memory cells and produce high levels of Type 1 cytokines, such as IL-2, IL-15, IFN-gamma, TNF-alpha and also express, preferably at high density, effector molecules such as CD40L, TRAIL and FasL on the cell surface but do not produce IL-4 or other Type 2 cytokines. CD40 ligation of innate immune cells (e.g., dendritic cells, macrophages and NK cells) has the capacity to induce high levels of the cytokine IL-12, which polarizes CD4+ T cells toward the Th1 type immunity, enhances proliferation of CD8+ T cells, and activates NK cells. These pro-inflammatory events can enable the consistent development of Th1 immunity to the alloantigens on the allogeneic cells upon rejection by the patient's immune system.

In the priming step, the activated allogeneic T-cells are administered to the patient, preferably intravenously, but can also be administered intradermally. The allogeneic cells are preferably derived from a deliberately HLA-mismatched donor. Preferred dosage in an aliquot of allogeneic cells for intravenous infusion is at least about $1 \times 10^7$ cells and more preferred is between about $1 \times 10^8$ to $1 \times 10^{10}$ cells. Dosages of allogeneic cells outside this range that can primarily generate an immune response are also within the scope of this invention.

It is desirable to test the patients for development of Th1 anti-alloantigen immunity prior to the ablation of affected tissue or administration of the antigenic composition. The development of Th1 anti-alloantigen immunity may take at least about 7 days. Preferably, the patient is allowed between about 7 days to about 14 days to develop Th1 anti-alloantigen immunity. The development of Th1 anti-alloantigen immunity can be measured by, for example, ELISPOT assay. Other methods of testing patients for development of Th1 anti-alloantigen immunity are also within the scope of this invention. If the Th1 anti-alloantigen immunity is weak, additional booster injections of allogeneic cells can be administered. Booster injections are preferably made intradermally to generate a delayed type hypersensitivity (DTH) reaction in the skin.

Generation of Allogeneic T-Cells

It is desirable that allogeneic T-cells can be generated such that, upon, activation and infusion into a patient, a Th-1 immunity can be generated by the patient. A preferred method for producing allogeneic cells with the properties necessary for stimulation of anti-allogeneic Th1 immunity involves: (1) the collection of mononuclear cell source material by leukapheresis from normal screened donors; (2) the isolation of CD4 T-cells from the source material; (3) the activation of the CD4+ cells with immobilized anti-CD3 and anti-CD28 monoclonal antibodies (mAbs) on days 0, 3 and 6; (4) the activation of the cells again on day 9 with immobilized anti-CD3 and anti-CD28 mAbs and the infusion of the cells within 24 h of activation.

Cell Death Step

In situ cell death or cell injury can result in recruitment of DC to the lesion and provide a source of antigen for uptake by DC. It is preferable that target tissues be destroyed by a process which causes death by necrosis. By necrosis it is meant the death of individual cells or groups of cells such that amounts of intracellular components are released to the environment. For purposes of this application, necrosis includes a cell death by a variety of methods including cryoablation, irreversible electroporation, chemotherapy, radiation therapy, ultrasound therapy, ethanol chemoablation, microwave thermal ablation, radio frequency energy or a combination thereof. Necrotically killed cells activate endogenous signals of distress responsible for the recruitment and maturation of DC, stimuli that would not be generated by healthy or apoptotically dying cells. Further, exposure of immature DC to these stimuli provides maturation signals, critical for the initiation of local and systemic Th1 immunity.

In one preferred embodiment, in order to cause death by necrosis, it is preferred that the target tissue is frozen in situ. Cryosurgery is a well-aimed and controlled procedure capable of inducing tissular necrosis by the application of liquid $N_2$ or argon gas. The biologic changes that occur during and after cryosurgery have been studied in vitro and in vivo. Tissue injury and necrosis is induced by cell freezing and by the vascular stasis that develops after thawing. Cryosurgery (in situ freezing) has been known to elicit an antigenic stimulus (comparable to that obtained through the parenteral administration of antigen) capable of generating a specific immunologic response against autologous antigens of the frozen tissue.

Cryoablation can cause peptides to be released from lysed tumor or pathogen-infected cells for antigen processing by DC and creates a pro-inflammatory cytokine environment. Cytokines released after cryoablation such as IL-1, IL-2, TNF-α, IFN-γ, and GM-CSF can activate the T, NK, and Langerhans cells essential to an immune response capable of destroying cancer or pathogen infected cells.

In another preferred embodiment, in order to cause death by necrosis, it is preferred that the target tissue is subject to irreversible electroporation. Irreversible electroporation is a tissue ablation technique in which micro to milli-second electrical pulses are delivered to the tissue to produce cell necrosis through irreversible cell membrane permeabilization. In irreversible electroporation, the cellular membranes of the cells between the electrodes are disrupted causing cellular necrosis. Irreversible electroporation can cause antigens to be released from lysed tumor or pathogen-infected cells for antigen processing by DC and creates a pro-inflammatory cytokine environment.

Another preferred method for generating a source of antigen is to isolate autologous chaperone proteins, also known as heat shock proteins (HSP), from dead infected tissue or tumors. HSPs are among the major targets of the immune response to bacterial, fungal and parasitic pathogens. Certain chaperones in extracellular milieu may also modulate innate and adaptive immunity due to their ability to chaperone polypeptides and to interact with the host's immune system, particularly professional antigen-presenting cells. Vaccination with heat shock proteins from tumor have been shown to elicit an anti-tumor response. Current studies indicate that the immunogenicity of HSPs is derived from the antigenic peptides with which they associate.

A preferred method for isolation of chaperone proteins for use as an antigen source is described by Katsantis in U.S. Pat. No. 6,875,849. Additional methods are described by Srivastava in U.S. Pat. Nos. 6,797,480; 6,187,312; 6,162,436; 6,139,841; 6,136,315; and 5,837,251.

Adjuvant Step

The purpose of the adjuvant step is to cause the maturation of DC to stimulate Th1 immunity against antigens taken up in the lesions containing dead target tissue. This can be accomplished by the injection of the same allogeneic cells, i.e. allogeneic cells of the same origin as those used to prime the patient. This aliquot of the allogeneic cells are, preferably, injected intralesionally, i.e. directly into the necrotic lesion caused by the cryoablation, or other method of cell death. Alternatively, when chaperone proteins are used as the source of antigen, the same allogeneic cells used to prime the patient are injected with the chaperone proteins, preferably intradermally. The dosage of the allogeneic cells to generate the desired immune response is generally at least about $1 \times 10^7$ cells and more preferred is between about $1 \times 10^8$ to $1 \times 10^{10}$ cells. Dosages of allogeneic cells outside this range that can generate the desired immune response are also within the scope of this invention. The preparation of the allogeneic cells is the same as described above.

To initiate an immune response and overcome the natural tolerance the immune system has to self tissues, the antigens released after necrotic cell death or associated with the chaperone proteins must be taken up by DC and presented with immune activating components that signal "danger". The memory immune response against the allogeneic cells create this "danger".

The tissue resident DC, termed immature DC, are able to capture the in situ generated antigens from the environment, but are deficient in stimulating T cells. In response to pathogen infection and the ensuing inflammatory response, DC undergo a differentiation process called maturation, whereby they up-regulate the capacity to migrate to draining lymph nodes and present the captured antigens to T cells. To activate Th1 $CD4^+$ T cells and CTL, the DC has to integrate a number of maturation/differentiation stimuli. At the site of pathogen or tumor encounter, exposure to pathogen or tumor-derived determinants, proinflammatory cytokines, and/or cell debris induces the first steps in the maturation process. This includes the up-regulation of costimulatory molecules and chemokine receptors, whereby the DC acquire the ability to present antigens to T cells and migrate to the lymph node, respectively. At the lymph node, encounter of cognate $CD4^+$ T cells provides additional differentiation stimuli to the DC, which regulate the survival of the activated T cells and the polarization of the $CD4^+$ T cells.

The maturation of DC occurs at the site of antigen uptake and the recall rejection response serves as an adjuvant to provide the appropriate inflammatory danger signals necessary for DC maturation, migration to the lymph nodes and the programming for Th1 immunity against the antigens uptaken in the lesion.

EXAMPLES

Animals

Balb/c mice were hosts and C57B1/6 (B6) mice were used as source of Th1 cells. All mice were 6 to 10 weeks old, were maintained in a specific pathogen-free facility at the Hadassah-Hebrew University Medical Center, and were treated on an approved animal protocol.

Preparation of Allogeneic Th1 Memory Cells

Spleen cells from male C57BL/6 mice were harvested and treated with ammonium chloride-potassium (ACK) buffer for lysis of red blood cells. Approximately 70-100 million cells were isolated per spleen. CD4+ T-cells were then purified by positive selection (purity >98%) using CD4 immunomagnetic particles on an MS column (Miltenyi Biotec, Germany), approximately 8-12 million CD4 cells were isolated with a yield of 50-60%. Th1 memory cells were generated by expansion with anti-CD3 and anti-CD28-coated paramagnetic beads (CD3/CD28 T-cell expander beads, Dynal/Invitrogen) at an initial bead:CD4 cell ratio of 3:1. The purified CD4 cells were incubated with 20 IU/mL recombinant mouse (rm)IL-2, 20 ng/mL rmIL-7, and 10 ng/mL rmIL-12 (Peprotech, N.J.) and 10 µg/mL antimurine IL-4 mAb (Becton Dickenson) in RPMI 1640 media containing 10% FBS, penicillin-streptomycin-glutamine, nonessential amino acids (NEAA) (Biological Industries, Israel) and 3.3 mM N-acetyl-cysteine (NAC; Sigma) (complete media). Additional cytokine-containing complete media with rmIL-2 and rmIL-7 was added to the CD4 cultures daily from days 3 to 6 to maintain the cell concentration between 0.5 and $1 \times 10^6$ cells/mL. Additional CD3/CD28 beads were added daily from day 3 to day 6. The number of beads added was calculated to maintain a 1:1 bead:cell ratio as the cells expanded. After 6 days in culture, the CD4 cells expanded approximately 80 to 100-fold and were harvested and debeaded by physical disruption and passage over a magnet. The phenotype of the harvested cells used in experiments were >95% CD4+, CD45RO+, $CD62L^{10}$, IFN-α+ and IL-4−.

CD3/CD28 Nanobead Preparation

Biotinylated mouse anti-CD3 and anti-CD28 mAbs (BD Pharmingen) were each diluted in 400 µl of PBS to a final concentration of 25 µl and then mixed in a 1:1 ratio so that the final volume was 800 µl of Strepavidin-coated nanobeads (Miltenyi, Germany) were washed and diluted to a final volume of 200 µl in PBS. The 800 µl of the CD3/CD28 mAb solution and the 200 µl of diluted nanobeads were then mixed so that the final concentration of each mAb was 0 µg/ml in a total volume of 1 ml. The mixture was placed on a rotating mixing device for 30 min at RT. The mAb conjugated nanobeads were then passed over an MS column (Miltenyi, Germany) on a magnet and washed thoroughly. The retained nanobeads were then released from the column and resuspended in 200 µl of PBS. The nanobeads were not able to activate naïve T-cells. Therefore, the nanobeads were tittered against harvested Th1 memory cells that had been previously activated 6 days prior with CD3/CD28 T-cell expander beads (Dynal, Norway). While there were slight variations per batch, generally 20 µl/$10^7$ cells was found to provide optimal activation of previously activated Th1 memory cells.

CD3/CD28 Cross-Linking

In experiments that required the infusion of activated Th1 memory cells, the harvested Th1 cells were incubated with a pre-tittered concentration of CD3/CD28-conjugated nanobeads prior to infusion. For optimal activation, the cells had to be incubated with the nanobeads for a minimum of 4 h and a maximum of 18 h. Optimal activation caused production of IFN-α and upregulation of CD40L and FasL on the cell surface. For these experiments, all infusions of CD3/CD28 cross-linked Th1 memory cells occurred after 4-8 h of pre-incubation. Cells were thoroughly washed prior to infusion to remove any unassociated nanobeads. Cross-linked Th1 memory cells used in these experiments expressed FasL and CD40L on the cell surface and produced in excess of 2000 ng/ml/$10^6$ cells/6 h IFN-α and less than 20 pg/ml IL-4 per $10^6$ cells/6 h. Th1 memory cells without CD3/CD28 cross-linking did not produce cytokines or express FasL or CD40L.

Cryotherapy

Cryotherapy was performed with a spherical nitrous oxide cryoprobe, 3 mm in diameter. The gas was maintained at a pressure of 50 bars and the Joule-Thomson effect allowed to attain temperatures ranging from −30 to −40° C. in the tissue. An incision was made in the centre of the tumor, the cryoprobe was placed in contact with the tumor (it was inserted 1-2 mm deep): the aim was to influence it by freezing but not to destroy it completely. Three cycles of rapid freezing (lasting for 20 s) followed by slow thawing were applied. The ice ball was produced at the center of the lesion and reached about two thirds of the total tumor volume.

Example #1

To test the ability of allogeneic Th1 cells to stimulate systemic anti-tumor immunity in extensive metastatic disease, the following protocol was tested. Lethal doses of tumor cells including BCL1 leukemia, 4T1 breast cancer and 3LL lung cancer were infused intravenously into mice on day 0 and the tumor cells were also injected intradermally to establish a solid tumor mass. On day 7, the mice were given a $1\times10^5$ dose of allogeneic Th1 cells. On day 14, the mice were treated intratumorally by injection of either: (a) saline; (b) saline+partial cryoablation of tumor; (c) allogeneic Th1 cells at a dose of $10^3$ cells; or (d) allogeneic Th1 cells+partial cryoablation of tumor. The results of surviving animals at 90 days is shown below (n=10):

| Intratumoral treatment | BCL1 Leukemia | 4T1 Breast | 3LL Lung |
|---|---|---|---|
| Saline | 0 (0%) | 0 (0%) | 0 (0%) |
| Saline + cryoablation | 0 (0%) | 0 (0%) | 0 (0%) |
| Th1 alone | 1 (10%) | 1 (10%) | 2 (20%) |
| Th1 + cryoablation | 4 (40%) | 5 (50%) | 8 (80%) |

Example #2

In order to investigate whether treatment of patients with solid tumors might benefit from the present invention, the experiment design above was repeated in animals that only received intradermal injections of tumors creating solid tumor masses. The results were similar to those obtained with animals with metastatic disease.

| Intratumoral treatment | BCL1 Leukemia | 4T1 Breast | 3LL Lung |
|---|---|---|---|
| Saline | 0 (0%) | 0 (0%) | 2 (20%) |
| Th1 alone | 0 (0%) | 0 (0%) | 1 (10%) |
| saline + cryoablation | 0 (0%) | 0 (0%) | 2 (20%) |
| Th1 + cryoablation | 6 (60%) | 7 (70%) | 9 (90%) |

The combination of Th1 cells with cryotherapy results in high cure rates. Cryotherapy kills tumors by necrosis, which is thought to be a more pathological type of cell death than death by apoptosis (the type of death caused by chemotherapy). It is thought that the cryotherapy makes the tumors more immunogenic and therefore the combination of allogeneic Th1 cells with necrotic tumor death creates a type of tumor vaccine leading to systemic anti-tumor immunity.

Although the present invention has been described with reference to preferred embodiments, workers skilled in the art will recognize that changes may be made in form and detail without departing from the spirit and scope of the invention.

What is claimed is:

1. A method of inducing an adaptive immune response against a tumor in a patient, the method comprising: generating antigens from the tumor in situ by ablation of the tumor, inducing necrotic death of tumor cells; and administering allogeneic T-cells to the site of the in situ generated antigens thereby creating an immune response that serves as an adjuvant to the uptake of antigens from the ablated tumor whereby subsequent maturation of the patient's antigen presenting cells systemically stimulate anti-tumor immunity.

2. The method of claim 1 further comprising:
   administering to the patient a priming composition prior to the generation of antigens in situ, the priming composition comprising allogeneic T-cells to be rejected by the patient's immune system in a manner that induces an allogeneic Th1 immunity; and
   permitting the patient's immune system to form anti-allogeneic Th1 immune memory prior to the generation of in situ antigens.

3. The method of claim 1 wherein the ablation is by cryoablation.

4. The method of claim 1 wherein the antigens comprise tumor antigens, heat shock proteins and combinations thereof.

5. The composition of claim 1 wherein the allogeneic cells express high levels of Type 1 cytokines.

6. The composition of claim 1 wherein the allogeneic cells express a high density of CD40L, TRAIL, FasL and combinations thereof on the cell surface.

* * * * *